United States Patent
Kawano et al.

(10) Patent No.: US 8,324,183 B2
(45) Date of Patent: Dec. 4, 2012

(54) MICRO-RNA ASSOCIATED WITH RHEUMATOID ARTHRITIS

(75) Inventors: Seiji Kawano, Hyogo (JP); Yuji Nakamachi, Hyogo (JP)

(73) Assignee: National University Corporation Kobe University, Hyogo (JP)

( * ) Notice: Subject to any disclaimer, the term of this patent is extended or adjusted under 35 U.S.C. 154(b) by 0 days.

(21) Appl. No.: 13/304,768

(22) Filed: Nov. 28, 2011

(65) Prior Publication Data

US 2012/0071541 A1    Mar. 22, 2012

Related U.S. Application Data

(62) Division of application No. 13/001,812, filed as application No. PCT/JP2009/053157 on Feb. 23, 2009, now abandoned.

(30) Foreign Application Priority Data

Jul. 3, 2008   (JP) ................................. 2008-174072

(51) Int. Cl.
   *C12N 15/11*    (2006.01)
   *A61K 48/00*    (2006.01)
   *C07H 21/02*    (2006.01)
   *C07H 21/04*    (2006.01)

(52) U.S. Cl. .................. 514/44 A; 514/44 R; 536/23.1; 536/24.5

(58) Field of Classification Search ........................ None
   See application file for complete search history.

(56) References Cited

U.S. PATENT DOCUMENTS

| | | | |
|---|---|---|---|
| 2005/0059005 A1 | 3/2005 | Tuschl et al. | |
| 2006/0019286 A1 | 1/2006 | Horvitz et al. | |
| 2009/0176723 A1* | 7/2009 | Brown et al. | 514/44 |

FOREIGN PATENT DOCUMENTS

| | | |
|---|---|---|
| EP | 2077326 A1 | 7/2009 |
| JP | 2006-510372 | 3/2006 |
| JP | 2008-511678 | 4/2008 |
| WO | 2004-057017 A2 | 7/2004 |
| WO | 2005-118806 A2 | 12/2005 |
| WO | 2006-028967 A2 | 3/2006 |
| WO | 2006-137941 A2 | 12/2006 |
| WO | 2008-029790 A1 | 3/2008 |

OTHER PUBLICATIONS

Nakasa et al., Expression of microRNA-146 n rheumatoid arthritis synovial tissue, 2008, Arthritis & Rheumatism, vol. 58, pp. 1284-1292.*
International Search Report for corresponding International Patent Application No. PCT/JP2009/053157 dated Apr. 28, 2009 (2 pages).
Furer et al., "The role of microRNA in rheumatoid arthritis and other autoimmune diseases," Clinical Immunology, vol. 136, 2010, pp. 1-15.
Ceribelli et al., "MicroRNAs in systemic rheumatic diseases," Arthritis Research & Therapy, vol. 13, 2011, pp. 1-10.

* cited by examiner

*Primary Examiner* — Dana Shin
(74) *Attorney, Agent, or Firm* — Kilyk & Bowersox, P.L.L.C.

(57) ABSTRACT

An object of the present invention is to provide a novel marker for rheumatoid arthritis (RA), and more specifically, to provide a marker whose expression may be specifically increased or decreased in RA. Another object of the present invention is to confirm whether or not miRNA serving as the marker is involved as the etiology of RA, and to provide an inspection method for RA and a therapeutic agent for RA each using the miRNA involved. The marker includes miRNA (for example, miR124a) whose expression is specifically increased or decreased in RA synovial cells based on a small RNA expression profile in the RA synovial cells. In addition, the therapeutic agent for RA includes miRNA (for example, miR124a) as an active ingredient.

4 Claims, 9 Drawing Sheets

THE MARK "*" MEANS THAT THERE IS A SIGNIFICANT DIFFERENCE

AFTER CULTURE OF RA FLS FOR 72 HOURS miR-124a: SYSTEM TRANSFECTED WITH pre-miR-124a
ng control: SYSTEM TRANSFECTED WITH CONTROL miRNA s
MICRO-RNA ASSOCIATED WITH RHEUMATOID ARTHRITIS This application is a divisional patent application of U.S. patent application Ser. No. 13/001,812 having a §371(c) date of Jan. 31, 2011, which is a National Phase Entry of and claims the benefit of earlier filed International Application No. PCT/JP2009/053157, filed Feb. 23, 2009, which claims priority to JP 2008-174072, filed Jul. 3, 2008.

TECHNICAL FIELD

The present invention relates to microRNA associated with rheumatoid arthritis (RA), and also relates to an inspection method for rheumatoid arthritis using the microRNA as an indicator and a therapeutic agent for rheumatoid arthritis containing the microRNA as an active ingredient.

BACKGROUND ART

Rheumatoid arthritis is a chronic, systemic, progressive autoimmune disease of unknown origin, which causes arthralgia (arthrosynovitis). In Japan, about 700,000 or more people suffer from the disease. Rheumatoid arthritis develops in people of any age, and more frequently develops in people who are in their thirties to fifties.

Genetic predisposition and environmental factors are presumably involved in the development of rheumatoid arthritis, but the etiology of rheumatoid arthritis remains unknown. Rheumatoid arthritis is a systemic disease in which CD4+ cells out of lymphocytes play a central role, and the pathology of rheumatoid arthritis includes the infiltration of inflammatory cells such as neutrophils, lymphocytes, and macrophages into the joint and the inflammatory abnormal growth of synovial cells in the joint in association with the infiltration, the subsequent development of cartilage destruction and bone erosion, and final joint structure destruction.

A diagnosis marker for rheumatoid arthritis is, for example, rheumatoid factor (RF), matrix metalloprotease-3 (MMP-3), or anti-cyclic citrullinated peptide antibody (anti-CCP antibody). The anti-CCP antibody is a serum diagnosis marker for rheumatoid arthritis, which has been developed in recent years. The antibody is said to be an excellent diagnosis method for rheumatoid arthritis as compared to a conventional diagnosis method, but is not a sufficiently satisfactory diagnosis method. In particular, rheumatoid arthritis is difficult to be diagnosed accurately at the early stage of the development. Thus, the importance of diagnosing rheumatoid arthritis at the early stage of the development and starting the treatment of rheumatoid arthritis at an earlier stage has been increasingly recognized.

Rheumatoid arthritis, the main symptom of which is polyarthralgia, is an inflammatory disease of unspecified origin. The progression of the pathology of rheumatoid arthritis is accompanied by the inflammatory infiltration of the synovial membrane, the growth and stratification of synovial cells, and angiogenesis. In particular, the abnormal growth or activation of synovial cells is thought to be one of the main lesions of rheumatism (Harriset et al., 1990, N. Eng. J. Med. 332, 1277-1289). When an investigation is made on the joint of patients with rheumatism, the growth of synovial villi, the multistratification of synovial tissue cells, and the like are observed, which suggests the abnormal growth of synovial cells. However, the cause of such hyperfunctions of synovial cells, which play important roles in forming the pathology of rheumatoid arthritis, has not been sufficiently elucidated yet, and the inhibition of the abnormal growth of synovial cells is conceivable to be extremely important in the treatment of rheumatoid arthritis.

A conventional treatment with an anti-rheumatic drug cannot completely inhibit the progression of arthritis, and there are many cases in each of which the treatment has no effect. Further, a biological formulation (anti-TNFα antibody), which has been developed in recent years, also has many problems. For example, there are cases in each of which the biological formulation has no effect or has a reduced effect, and high treatment costs are required. Accordingly, it is medically and socially important to clarify the etiology of rheumatoid arthritis and develop novel methods for diagnosis and treatment of rheumatoid arthritis.

Along with the elucidation of the genetic information of living organisms, it has been revealed that the ratio of non-coding DNA which does not encode for a protein is very high in higher living organisms. The non-coding DNA is said to account for 98.3% of the total DNA in humans. Further, as RNA is estimated to be transcribed from two-thirds of the total genome in humans, the kinds and amount of non-coding RNAs are estimated to increase depending on the complexity of biological species, and microRNA (hereinafter referred to as "miRNA") has been discovered as one of the non-coding RNAs. The miRNA is a generic name for the non-coding RNAs having 18 to 22 bases, and about one-third of human genes are thought to be regulated by the miRNA. Various reports have already been made on the processing of the miRNA. The miRNA is expressed and highly conserved in eukaryotes. About 1000 kinds of miRNAs are estimated to exist in humans. With regard to the miRNA, JP 2006-510372 A (Patent Document 1) discloses a detection method for a low molecular nucleic acid.

The miRNA plays an important role in regulating the expression of genes. The miRNA is transcribed as pri-miRNA from DNA in the nucleus to be processed into hairpin double-stranded RNA (dsRNA) precursor. dsRNA is translocated to the cytoplasm and undergoes an action of Dicer to produce mature miRNA. The produced miRNA is incorporated into an RNA-induced silencing complex (RISC) and is involved in the regulation of gene function. The miRNA has a very similar action to that of RNA interference (RNAi) or the like, but many of the actions are unclear. For example, the RNAi inhibits translation by cleaving a target RNA, whereas most of the miRNAs are thought to inhibit translation without cleaving the target RNA. Further, there are reports that the miRNA may be involved in, for example, development, differentiation, cell cycles, and cancer diseases, and it has been revealed that each of tumor types can be distinguished from a normal sample based on specific miRNA in tumor tissues of patients with, for example, lung cancer, colon cancer, thoracic cancer, prostate cancer, bladder cancer, and pancreas cancer (Patent Document 2).

However, with regard to the miRNA, there are little reports on an immune system and an autoimmune disease, and there are no reports on rheumatoid arthritis at present.
Patent Document 1: JP 2006-510372 A
Patent Document 2: JP 2008-511678 A

DISCLOSURE OF THE INVENTION

Problems to be Solved by the Invention

An object of the present invention is to provide a novel marker for rheumatoid arthritis, and more specifically, to provide a marker whose expression may be specifically increased or decreased in rheumatoid arthritis. Another object of the present invention is to confirm whether or not miRNA serving as a marker is involved as the etiology of rheumatoid arthritis, and to provide an inspection method for rheumatoid arthritis and a therapeutic agent for rheumatoid arthritis each using the miRNA involved.

Means for Solving the Problems

In order to solve the above-mentioned problems, the inventors of the present invention have focused on small RNA in synovial cells in the joint with rheumatoid arthritis (also referred to as "RA synovial cells") and have made extensive studies. As a result, the inventors have first found the presence of miRNA whose expression is specifically increased or decreased in RA synovial cells based on a miRNA expression profile. Thus, the present invention has been completed.

That is, the present invention includes the following:
1. a marker for rheumatoid arthritis, including non-coding RNA whose expression is specifically suppressed in rheumatoid arthritis;
2. a marker for rheumatoid arthritis according to the item 1, in which the non-coding RNA includes microRNA (miRNA);
3. a marker for rheumatoid arthritis according to the item 2, in which the microRNA (miRNA) includes miR-124a;
4. a marker for rheumatoid arthritis according to the item 1 or 2, in which the marker for rheumatoid arthritis has a base sequence selected from the following:

(1) UUAAGGCACGCGGUGAAUGCCA;   (SEQ ID NO: 1)

and
(2) a base sequence having substitutions, deletions, additions, or insertions of one or two nucleotides in an oligonucleotide formed of a base sequence according to the above-mentioned item (1);
5. an inspection method for rheumatoid arthritis, including using as an indicator the marker for rheumatoid arthritis according to any one of the items 1 to 4;
6. an inspection method for rheumatoid arthritis, including the following steps:
(1) quantifying a marker for rheumatoid arthritis (A) in a collected biological sample using the marker for rheumatoid arthritis according to any one of the items 1 to 4 as an indicator; and
(2) comparing a quantitative value for the marker for rheumatoid arthritis (A) quantified as described above to a quantitative value for a marker for rheumatoid arthritis (B) in a biological sample free from rheumatoid arthritis;
7. an inspection method for rheumatoid arthritis according to the item 6, in which the quantitative values for the marker for rheumatoid arthritis (A) and the marker for rheumatoid arthritis (B) represent amounts of oligonucleotides as those markers;
8. an inspection method for rheumatoid arthritis according to the item 6 or 7, including making the diagnosis of rheumatoid arthritis when the quantitative value for the marker for rheumatoid arthritis (A) is lower than the quantitative value for the marker for rheumatoid arthritis (B);
9. a therapeutic agent for rheumatoid arthritis, including, as an active ingredient, an oligonucleotide formed of a base sequence selected from the following:

(1) UUAAGGCACGCGGUGAAUGCCA;   (SEQ ID NO: 1)

and
(2) a base sequence having substitutions, deletions, additions, or insertions of one or two nucleotides in an oligonucleotide formed of a base sequence according to above-mentioned item (1); and
10. a therapeutic agent for rheumatoid arthritis, including, as an active ingredient, an oligonucleotide that forms miR-124a.

Effects of the Invention

The marker for rheumatoid arthritis of the present invention is non-coding RNA whose expression is specifically increased or decreased in rheumatoid arthritis. In particular, mi-RNA (miR-124a) whose expression is suppressed directly acts on mRNAs of cyclin-dependent kinase (CDK) 2, CDK6, and monocyte chemotactic protein-1 (MCP1). The fact has confirmed that the non-coding RNA serving as the marker for rheumatoid arthritis of the present invention is involved in cell cycles and the expression of an inflammation-associated protein. It is conceivable that CDK2, CDK6, and MCP1 act on RA synovial cells through the suppression of the expression of the non-coding RNA serving as the marker for rheumatoid arthritis of the present invention, which may be associated with the pathology of rheumatoid arthritis. An oligonucleotide that forms the non-coding RNA of the present invention regulates the expression of CDK2, CDK6, and MCP1, suppresses the inflammation and growth of RA synovial cells attributed to those proteins, and thus acts as an active ingredient for the treatment of rheumatoid arthritis.

BEST MODE FOR CARRYING OUT THE INVENTION

Figure 1:
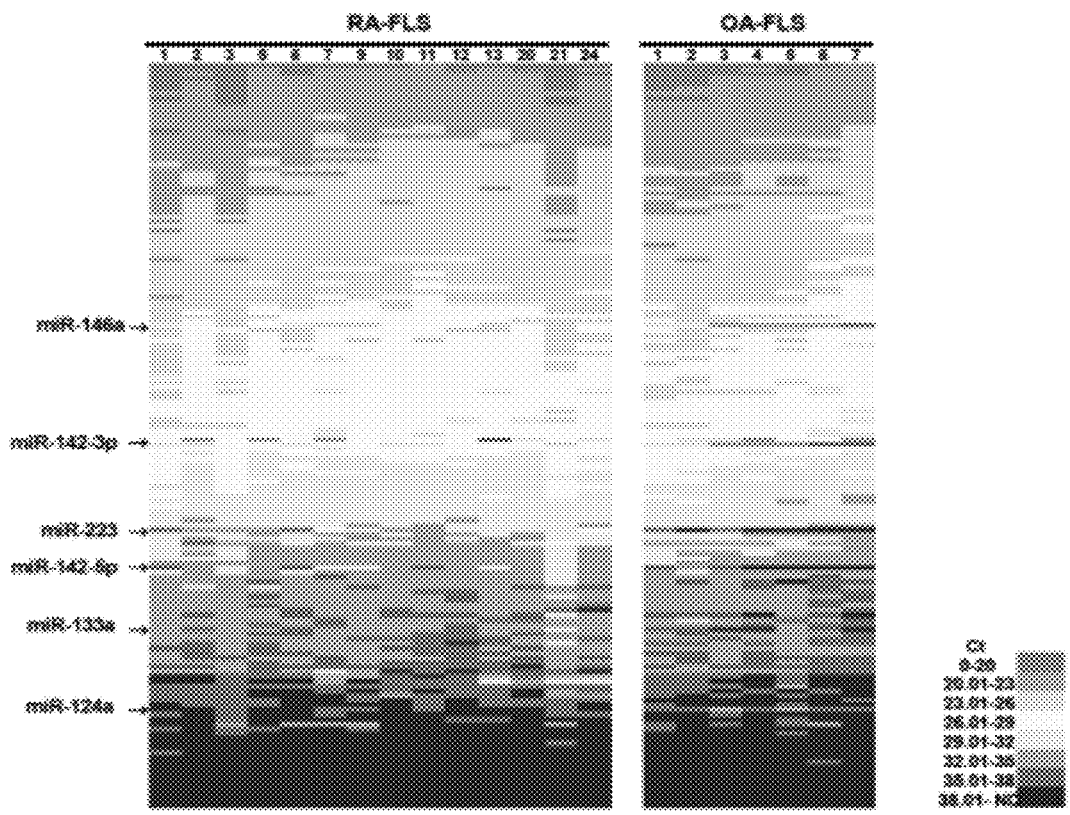
FIG. 1 are views illustrating expression patterns of mi-RNAs in rheumatoid arthritis-derived synovial cells (RA-FLS) and osteoarthritis-derived synovial cells (OA-FLS) (Reference Example 1).

In the present invention, rheumatoid arthritis (which may hereinafter be simply referred to as "RA") is a disease defined in the Annual General Assembly of the Japan College of Rheumatology and the Ministry of Health, Labour and Welfare. The synovial membrane refers to a tissue closest to the side of the joint out of connective tissues that cover the interior of the joint, and has roles in removing wastes generated in the joint and secreting synovial fluid. In the case of rheumatoid arthritis, an inflammation occurs in the synovial membrane, and the growth of lining cells is observed at the early stage.

The inventors of the present invention have focused on small RNA in synovial cells with rheumatoid arthritis (RA) and osteoarthritis (degenerative joint disease; OA, which may hereinafter be simply referred to as "OA") and have further analyzed RNAs having different expression amounts in both diseases to obtain a marker for rheumatoid arthritis including non-coding RNA of the present invention. The marker for rheumatoid arthritis is formed of small RNA whose expression is specifically suppressed in rheumatoid arthritis. The small RNA is an oligonucleotide having 18 to 200 bases, and is non-coding RNA having preferably 18 to 50 bases, more preferably 18 to 22 bases. Such oligonucleotide is, for example, miRNA, more specifically miR-124a (SEQ ID NO: 1) or miR-124 (SEQ ID NO: 10). A specific example thereof is an oligonucleotide formed of the following base sequence, and miR-124 (SEQ ID NO: 10) has deletions of the 1st and 22nd nucleotides (bases U and A) in an oligonucleotide set forth in SEQ ID NO: 1.

(1) UUAAGGCACGCGGUGAAUGCCA (SEQ ID NO: 1)

(2) a base sequence having substitutions, deletions, additions, or insertions of one or two nucleotides in an oligonucleotide formed of a base sequence according to the above-mentioned item (1)

```
(3) UAAGGCACGCGGUGAAUGCC.    (SEQ ID NO: 10)
```

The present invention also encompasses an inspection method for rheumatoid arthritis, in which the above-mentioned marker for rheumatoid arthritis is used as an indicator. Specifically, rheumatoid arthritis may be inspected by quantifying the amounts of oligonucleotides as the above-mentioned markers for rheumatoid arthritis in synovial cells of a subject. For example, rheumatoid arthritis may be inspected by detecting the marker for rheumatoid arthritis of the present invention, e.g., miR-124a whose expression is suppressed with respect to the amount of a marker in synovial cells of a human not suffering from rheumatoid arthritis. The degree of expression suppression is not particularly limited. For example, there is included a case where the expression is suppressed by a factor of two or more as compared to a case where rheumatoid arthritis is not expressed.

The inspection method for rheumatoid arthritis is, for example, an inspection method including the following steps:

(1) quantifying a marker for rheumatoid arthritis (A) in a collected biological sample using the above-mentioned marker for rheumatoid arthritis as an indicator; and (2) comparing a quantitative value for the marker for rheumatoid arthritis (A) quantified as described above to a quantitative value for a marker for rheumatoid arthritis (B) in a biological sample free from rheumatoid arthritis.

Here, an example of the collected biological sample according to the marker for rheumatoid arthritis (A) is a sample collected from a subject. Specifically, in the above-mentioned example, synovial cells derived from a subject in need of diagnosis for rheumatoid arthritis may be used as the biological sample. The synovial cells may be acquired by an acquiring method known per se. The biological sample free from rheumatoid arthritis according to the marker for rheumatoid arthritis (B) is a biological sample obtained from a subject clearly diagnosed not to have rheumatoid arthritis. Specific example thereof includes synovial cells obtained from a patient with osteoarthritis.

The quantitative values for the marker for rheumatoid arthritis (A) and the marker for rheumatoid arthritis (B) may be determined by quantifying the amounts of oligonucleotides as those markers. Specifically, the quantitative values may be determined by a ΔCt method after measuring the number of cycles required for the amplification of the marker for rheumatoid arthritis of the present invention in a given amount by a real-time RT-PCR method or a stem-loop RT-PCR method.

During the inspection of rheumatoid arthritis, in the above-mentioned example, a subject can be diagnosed to have rheumatoid arthritis when the quantitative value for the marker for rheumatoid arthritis (A) is lower than the quantitative value for the marker for rheumatoid arthritis (B).

The present invention also encompasses a therapeutic agent for rheumatoid arthritis, including, as an active ingredient, an oligonucleotide formed of the following base sequence. Specifically, the therapeutic agent includes, as an active ingredient, an oligonucleotide formed of a base sequence substantially equivalent to the marker for rheumatoid arthritis of the present invention. The sequence is substantially equivalent to an oligonucleotide that forms miR-124a (SEQ ID NO: 1), and more specifically, is an oligonucleotide formed of the following base sequence. The sequence may be an oligonucleotide that forms a precursor of each of those oligonucleotides as long as the sequence includes an oligonucleotide having the following base sequence. Specific examples thereof may include an oligonucleotide that forms pre-miR-124a or pre-miR-124.

```
(1) UUAAGGCACGCGGUGAAUGCCA    (SEQ ID NO: 1)
```

(2) a base sequence having substitutions, deletions, additions, or insertions of one or two nucleotides in an oligonucleotide formed of a base sequence according to the above-mentioned item (1).

The above-mentioned oligonucleotide is involved in cell cycles and the expression of an inflammation-associated protein. It is conceivable that MCP1, which is an inflammation-associated protein, and CDK2 and CDK6, which function throughout the G1 phase to the S phase in the cell cycles, act on RA synovial cells through the suppression of the expression of the oligonucleotide as the non-coding RNA serving as the marker for rheumatoid arthritis of the present invention, which may be associated with the pathology of rheumatoid arthritis. The above-mentioned oligonucleotide regulates the expression of CDK2, CDK6, and MCP1, suppresses the inflammation and growth of RA synovial cells attributed to those proteins, and thus acts as an active ingredient for the treatment of rheumatoid arthritis.

The therapeutic agent for rheumatoid arthritis of the present invention may be administered to a patient by formulating an oligonucleotide as an active ingredient with, for example, a pharmaceutically acceptable carrier, diluent, excipient, and stabilizing agent. For this purpose, a formulation aid well known to a person skilled in the art may be utilized. The therapeutic agent for rheumatoid arthritis of the present invention can be expected to achieve a desirable therapeutic effect through the setting of a preferred administration route such as intravenous administration or oral administration or the other administration modalities. Further, a composition for gene therapy may be prepared by using, as a therapeutic gene, an oligonucleotide used for the therapeutic agent for rheumatoid arthritis of the present invention in combination with a carrier designed for the treatment described above. In addition, a method known per se such as a method using a virus vector such as an adenovirus vector may be utilized for gene therapy.

EXAMPLES

In order to aid the understanding of the present invention, the present invention is specifically described below by way of a reference example contributing to the completion of the present invention and further examples. It goes without saying that the present invention is by no means limited to the examples.

Reference Example 1

Expression Profile of miRNA in RA Synovial Cells

Synovial cells were obtained through the approval of an ethics committee from a patient with RA diagnosed in conformity with the standard of the American College of Rheumatology and a patient with osteoarthritis (OA) as a control who had given informed consent (RA synovial cells (RA-FLS) and OA synovial cells (OA-FLS)). Each of the cells were cultured and maintained in an RPMI medium containing 10% FCS and 4 mM L-glutamine. Small RNAs having 200 bases or less were extracted from the above-mentioned cells (mirVana™ miRNA Bioarrays, manufactured by Ambion) to perform miRNA expression analysis. The small RNAs were extracted in accordance with a method known per se. The extracted 156 kinds of miRNAs were subjected to quantification by real-time RT-PCR (TaqMan® MicroRNA Assays manufactured by Applied Biosystems) and a ΔCt method.

The results confirmed that six kinds of miRNAs different by a factor of two or more in expression amount between RA-FLS and OA-FLS were detected, five kinds thereof had enhanced expression in RA-FLS and one kind thereof had decreased expression (Table 1 and FIG. 1). Of those, miRNA that had decreased expression in RA-FLS was miR-124a.

TABLE 1

| | median (Ct) | | | | |
|---|---|---|---|---|---|
| | RA-FLS n = 14, | OA-FLS n = 7 | ΔCt | fold change | P value |
| hsa-miR-146a | 26.4 | 32.2 | −5.8 | 55.2 | 0.000 |
| hsa-miR-223 | 31.3 | 38.9 | −7.6 | 188.9 | 0.001 |
| hsa-miR-142-3p | 28.4 | 33.5 | −5.2 | 35.5 | 0.001 |
| hsa-miR-142-5p | 33.0 | 38.2 | −5.2 | 37.7 | 0.002 |
| hsa-miR-133a | 34.6 | 36.5 | −1.9 | 3.7 | 0.007 |
| hsa-miR-124a | 38.3 | 35.7 | 2.6 | 6.3 | 0.009 |

Example 1

Expression of miRNA in RA-FLS 300 pmol of pre-miR-124a or control pre-miRNA (Ambion) were added to 1 mL of an OptiMEM medium (Invitrogen) together with 10 μL of RNAiMAX (Invitrogen). After that, the mixture was added to a plate having a size of 60 mm, and the temperature was kept at room temperature for 20 minutes. After that, 5 ml of an RA-FLS cell suspension ($1 \times 10^5$ cells/ml) in an RPMI medium were seeded to the plate, and the mixture was cultured in a $CO_2$ incubator for 24 to 96 hours. Quantification was performed by miR-124a-specific real-time RT-PCR (TaqMan® MicroRNA Assays, manufactured by Applied Biosystems) and a ΔCt method.

Figure 2:
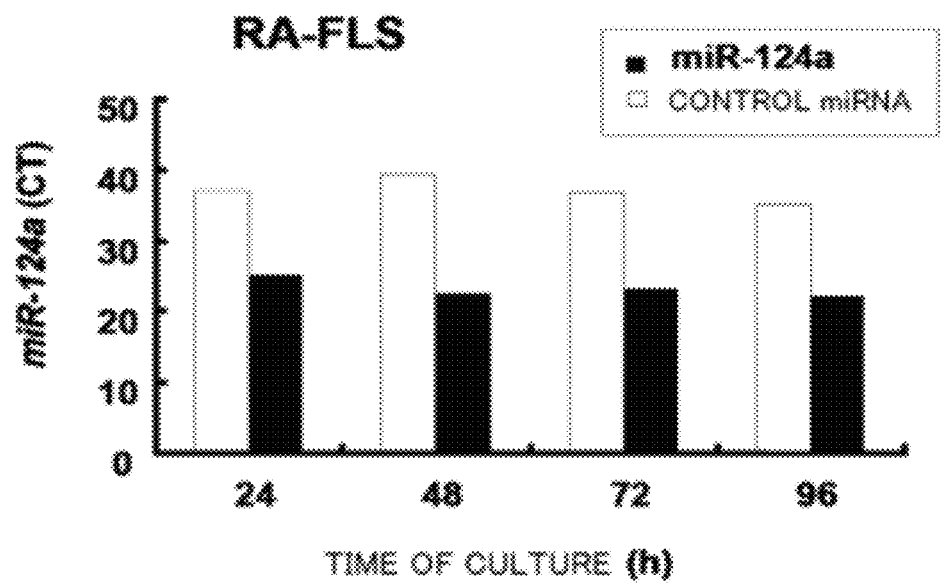
FIG. 2 is a graph illustrating expression amounts of miR-124a in cells in the case where RA-FLS is transfected with pre-miR-124a or control pre-miRNA and cultured for 24 to 96 hours (Example 1).

The results confirmed that the expression amount of miR-124a was high as compared to the expression amount of control miRNA in each time of culture as a result of the addition of an equal amount of pre-miRNA (FIG. 2).

Experimental Example 1

Influences of miR-124a on Growth of Various Cells

Influences of miR-124a on the growth of various cells were examined.

In the same manner as in Example 1, an examination was made on influences on the growth of cells in the case where the respective cells, OA-FLS (n=2), RA-FLS (n=4), E11 cells, and HeLa cells were transfected with 300 pmol of pre-miR-124a or control pre-miRNA (Ambion) and cultured in a $CO_2$ incubator for 24 to 96 hours.

Figure 3:
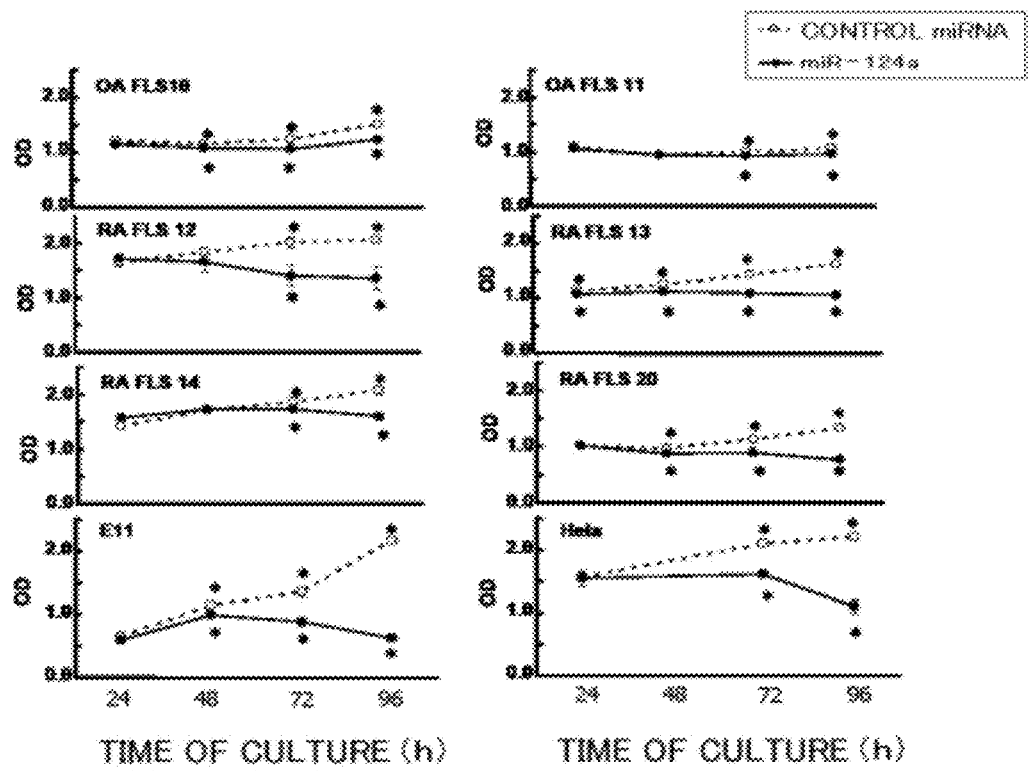
FIG. 3 are graphs illustrating influences on the growth of cells in the case where RA-FLS, OA-FLS, E11 cells, and HeLa cells are transfected with miR-124a (XTT method) (Experimental Example FIG. 4 is a graph illustrating an influence on the growth of cells in the case where RA-FLS is transfected with miR-124a (Experimental Example 1).

The measurement results of the degree of the growth of cells by an XTT method using a Cell Proliferation Kit II (manufactured by Roche Applied Science) confirmed that the growth of cells was clearly suppressed in RA-FLS, OA-FLS, E11, and HeLa cells, transfected with pre-miR-124a (FIG. 3).

Figure 4:
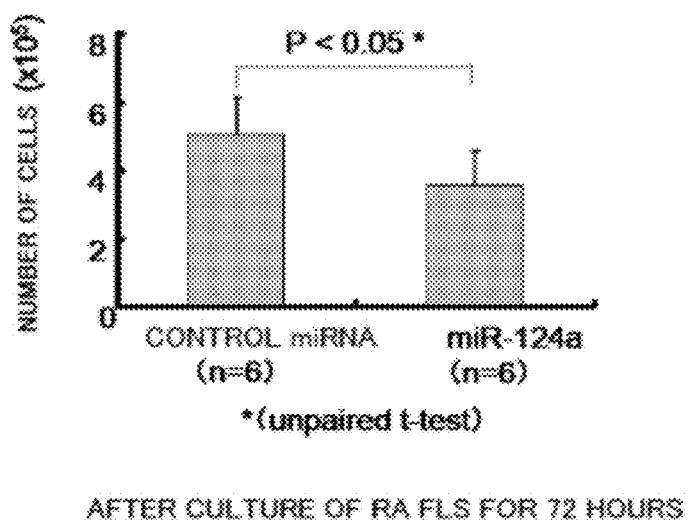

Also in the case where the number of cells was measured by a trypan blue method, as illustrated in FIG. 4, it was confirmed that, in RA-FLS cells, the growth of cells was clearly suppressed in the cells transfected with pre-miR-124a.

Figure 5:
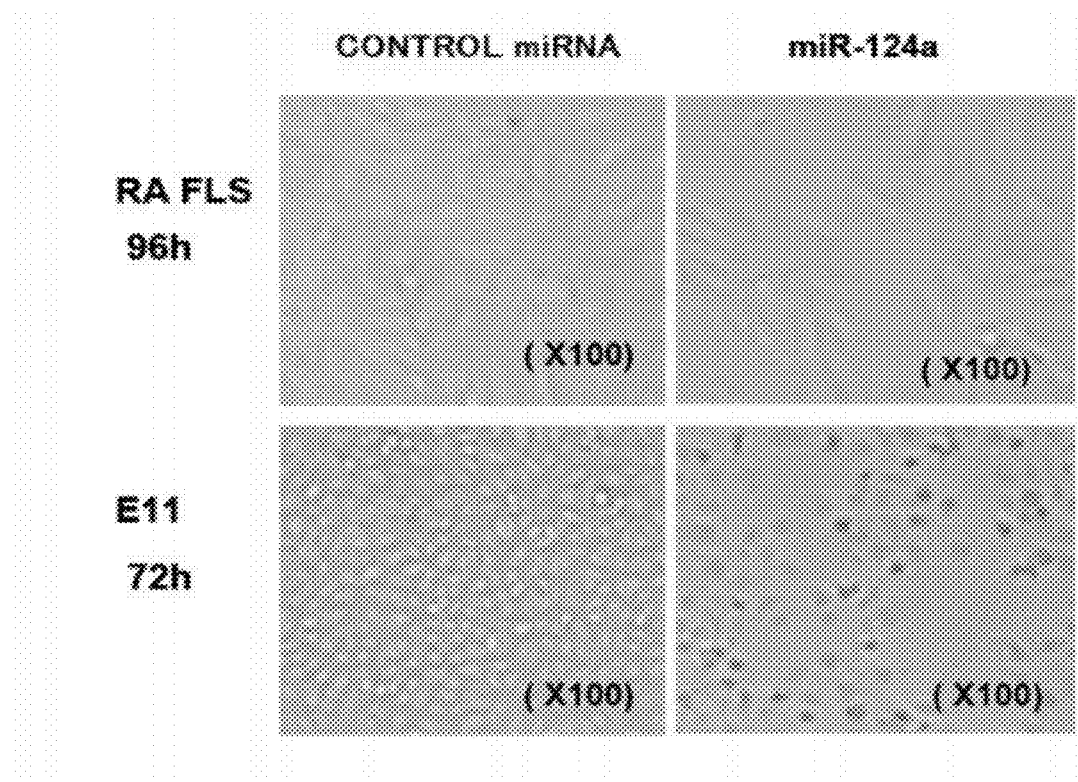
FIG. 5 are photographs each showing culture states in the case where RA-FLS or E11 cells are transfected with miR-124a and then cultured for 96 hours for the RA-FLS or for 72 hours for the E11 cells (Experimental Example 1).

Further, FIG. 5 show photographs in the case where the degree of the growth of each of RA-FLS cells after culture for 96 hours and E11 cells after culture for 72 hours was observed with a microscope. The results also confirmed that the growth of cells was clearly suppressed in the cells transfected with pre-miR-124a, and in particular, detachment was about to occur in the E11 cells (adhesive cells).

Experimental Example 2

Influences of miR-124a on Cell Cycles of Various Cells

Influences of miR-124a on the respective cell cycles were examined.

In the same manner as in Example 1, an examination was made on influences on cell cycles in the case where RA-FLS and E11 cells were transfected with 300 pmol of pre-miR-124a or control pre-miRNA (Ambion) and cultured in a $CO_2$ incubator for 72 hours. The cell cycles (G1 phase, S phase, and G2 phase) were subjected to staining with a PI/RNase staining (Becton, Dickinson and Company) and analyzed with Modifit software (Becton, Dickinson and Company).

Figure 6:
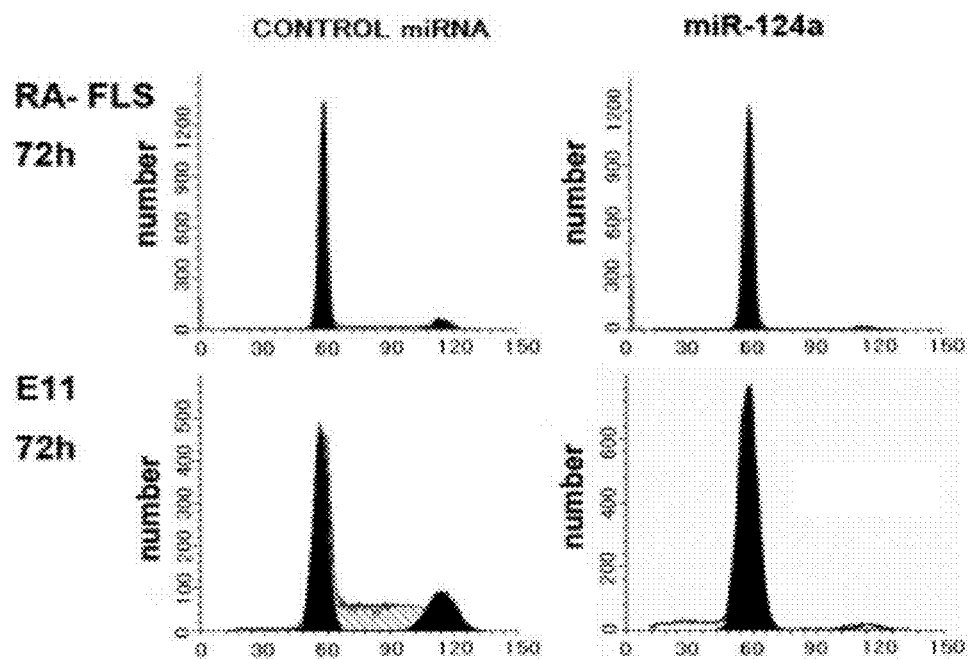
FIG. 6 are graphs illustrating influences of miR-124a on the cell cycles of RA-FLS or E11 cells (Experimental Example 2).
Figure 7:
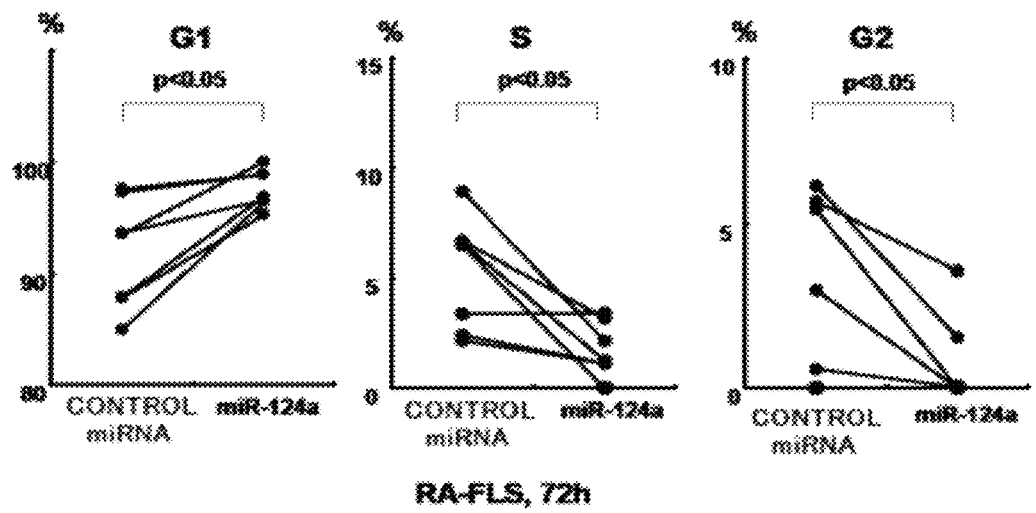
FIG. 7 are graphs illustrating influences of miR-124a on the cell cycles of RA-FLS (Experimental Example 2).

The results confirmed that, after culture for 72 hours, the number of cells at the G1 phase was large and the number of cells at the G2 phase/S phase was small in both RA-FLS and E11 cells transfected with pre-miR-124a (FIG. 6 and FIG. 7).

Experimental Example 3

Influences of miR-124a on Apoptosis of Cells

Influences of miR-124a on the apoptosis of RA-FLS were examined.

In Experimental Example 2, the apoptosis of RA-FLS was confirmed by staining with Annexin V and PI. Annexin V-positive and PI-negative cells were assessed to be initial apoptosis. The staining with Annexin V was performed with an MEBCYTO apoptosis kit (manufactured by Medical & Biological Laboratories Co., Ltd. (MBL)).

Figure 8:
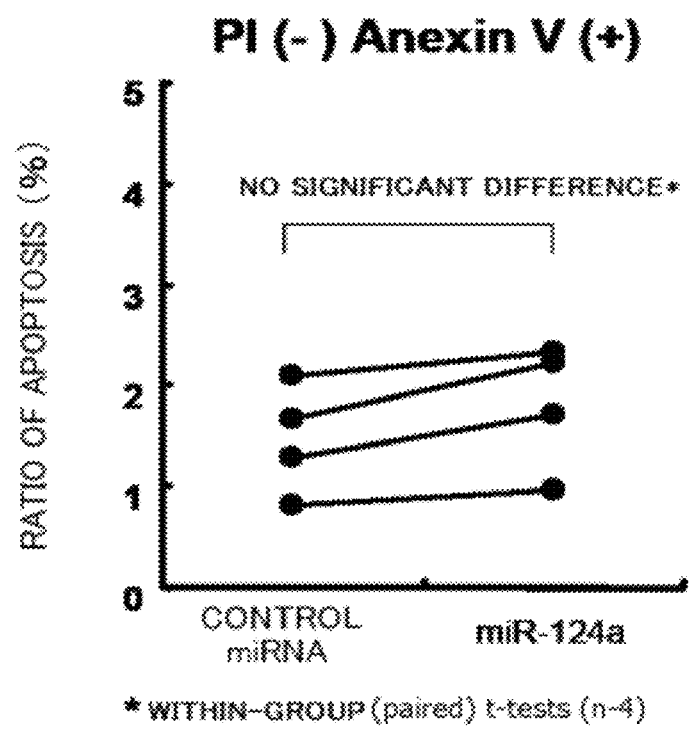
FIG. 8 is a graph illustrating an influence of miR-124a on the apoptosis of RA-FLS (Experimental Example 3).
Figure 9:
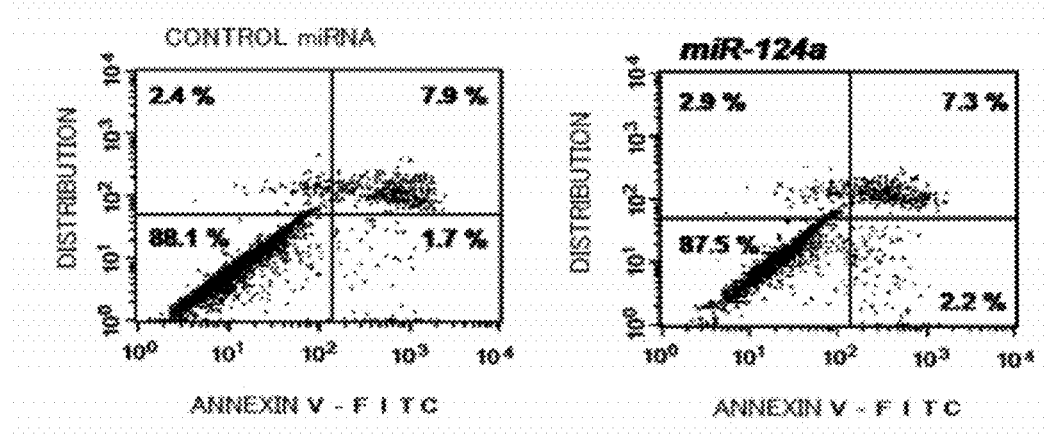
FIG. 9 are graphs illustrating influences of miR-124a on the apoptosis of RA-FLS (Experimental Example 3).
Figure 10:
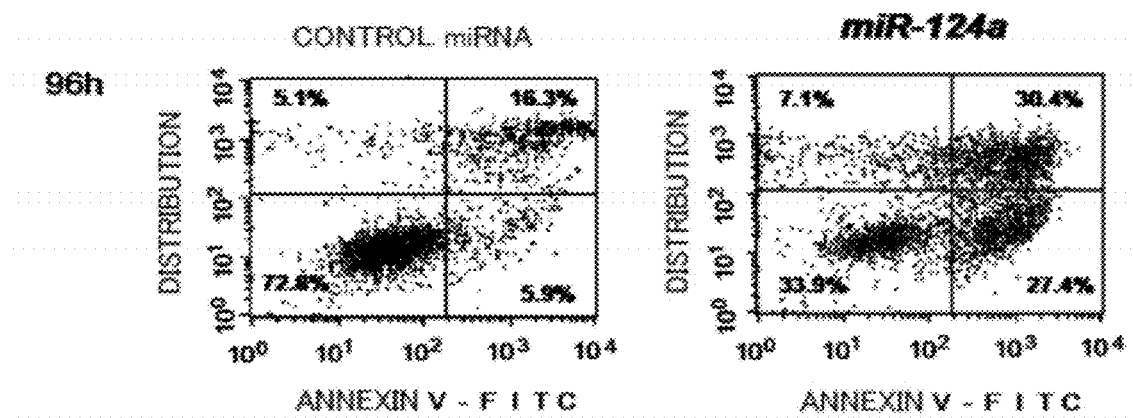
FIG. 10 are graphs illustrating influences of miR-124a on the apoptosis of E11 cells (Experimental Example 3).

The results confirmed that there was no significant difference from a control in the degree of apoptosis in the transfection with pre-miR-124a in RA-FLS (FIG. 8 and FIG. 9), whereas apoptosis was induced in E11 cells (FIG. 10).

Experimental Example 4

Influences (1) of miR-124a on Expression of CDK2 in Cells

A study was made to determine what protein in cells is affected by miR-124a to arrest cell cycles at the G1 phase and suppress the growth of cells. Here, the study was made with a focus on a CDK2 protein which functions throughout the G1 phase to the S phase. The expression of the CDK2 protein in RA-FLSs (five kinds) and OA-FLSs (four kinds) was analyzed by a western blotting method. The mouse anti-human CDK2 antibody clone used was one manufactured by Santa Cruz Biotechnology, Inc. The expression amount of actin serving as a housekeeping protein for confirming the expression of the protein was also confirmed. For each of the cells, the expression of miR-124a was measured by a real-time RT-PCR method and quantified by a ΔCt method.

Figure 11:
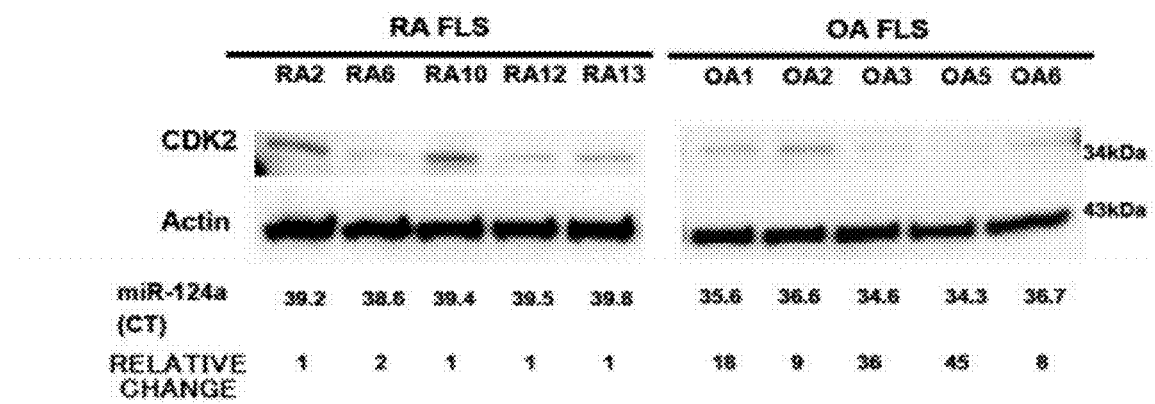
FIG. 11 are photographs showing influences of miR-124a on the expression of CDK2 in various RA-FLSs and OA-FLSs (Experimental Example 4).
Figure 12:
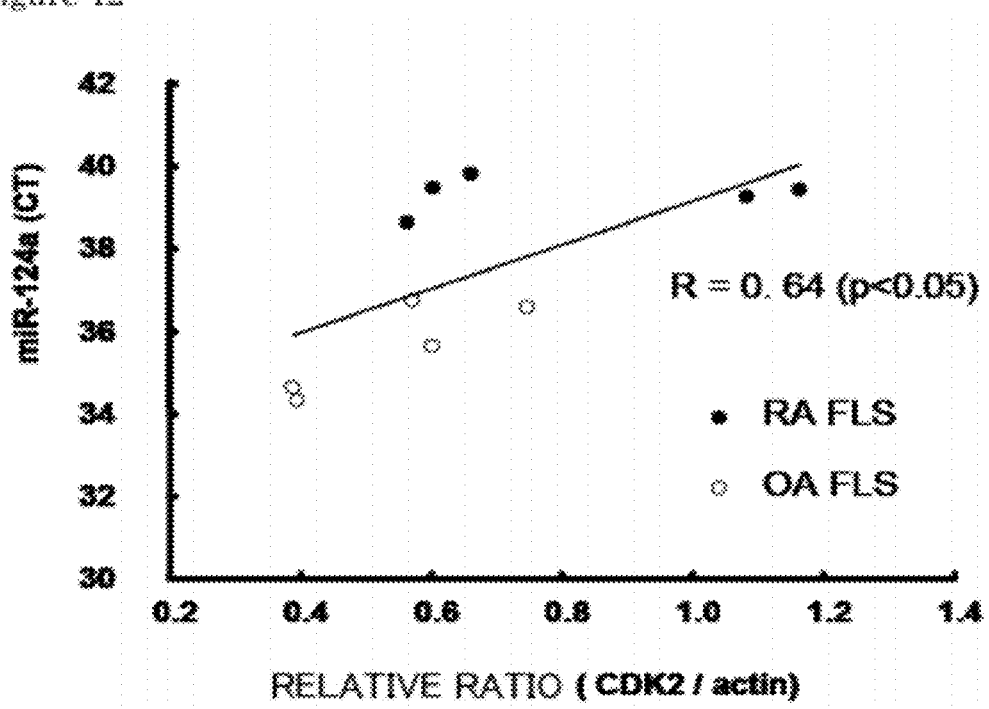
FIG. 12 is a graph illustrating influences of miR-124a on the expression of CDK2 in various RA-FLSs and OA-FLSs (Experimental Example 4).

The results confirmed that, when the expression of CDK2 was analyzed by a western blotting method, a stronger band was detected in RA-FLS than in OA-FLS, and the expression amount of CDK2 was higher in RA-FLS (FIG. 11). Further, when the expression level of miR-124a was confirmed for each of the cells, the expression level was lower in RA-FLS than in OA-FLS, and the following tendency was confirmed: as the expression level of miR-124a was lower, the expression amount of the CDK2 protein was higher (FIG. 12). The fact suggested that miR-124a affected the expression of CDK2, and the growth of synovial cells was activated in RA-FLS because CDK2 was richer in RA-FLS than in OA-FLS.

Experimental Example 5

Influences (2) of miR-124a on Expression of CDK2 in Cells

Influences on the expression of a CDK2 protein in the case where RA-FLS cells and E11 cells were transfected with pre-miR-124a in the same manner as in Example 1 and Experimental Example 1, and cultured in a $CO_2$ incubator for 72 hours were examined by a western blotting method.

Figure 13:
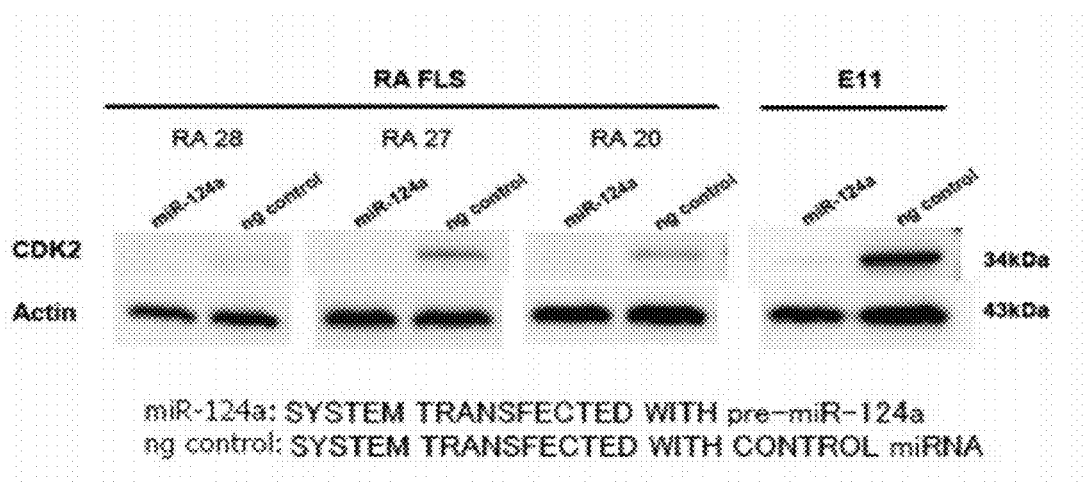
FIG. 13 are photographs showing influences of miR-124a on the expression of CDK2 in various RA-FLSs (Experimental Example 5).

The results confirmed that the expression of CDK2 was suppressed in each of the cells transfected with pre-miR-124a as compared to the control (FIG. 13). The fact also suggested that miR-124a was involved in the expression of CDK2.

Experimental Example 6

Influences (3) of miR-124a on Expression of CDK2

A study was made to determine whether or not miR-124a directly acted on the 3'-untranslated region (3'UTR) of CDK2 mRNA to decrease the expression amount of a CDK2 protein. The study was made by incorporating the 3'UTR of CDK2 DNA into a luciferase expression vector (psiCHECK™ vector (Promega)) and introducing the resultant into E11 cells. As for systems transfected with various pre-miRNAs, the expression of luciferase was measured based on a luciferase activity. A luciferase activity was also measured in each of controls, i.e., a system in which part of genes in the 3'UTR of CDK2 DNA were altered (mutant-type), a system in which no pre-miRNA was added, a system in which control pre-miRNA was added in the same manner as in Example 1, and a system in which another pre-miRNA (pre-miR-146) was added.

CDK2 DNA is as set forth in GenBank accession No. AF512553, and the 3'UTR portion (Positions 5281 to 6439) of CDK2 wild-type DNA was amplified by a PCR method using primers having sequences set forth in the following SEQ ID NOS:

```
CDK2-F-XhoI:
CTCGAGcccttcttccaggatgtga         (SEQ ID NO: 2)
(based on 5232 to 5251);
and CDK2-R-NotI:
GCGGCCGCtgttcaccgtcagcactagc      (SEQ ID NO: 3)
(based on 6592 to 6573).
```

The 3'UTR portion of CDK2 mutant-type DNA was produced by a PCR method using primers having the following sequences:

```
CDK2-3'UTR-mut-F:
tgaacttCGcttaaacactcaccttct;      (SEQ ID NO: 4)
and

CDK2-3'UTR-mut-R:
tttaagCGaagttcagagggcccacc.       (SEQ ID NO: 5)
```

Figure 14:
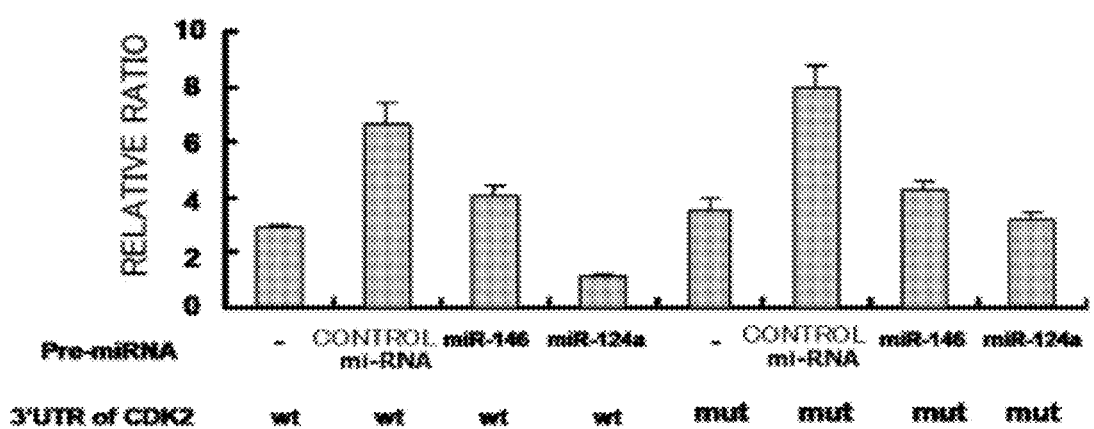
FIG. 14 is a graph illustrating influences of miR-124a on an mRNA non-coding 3'-region of CDK2 (Experimental Example 6).

Measurement results under the respective conditions were each expressed as a relative ratio with respect to a luciferase activity for a control, which had been incorporated into a vector, defined as 1 (FIG. 14). The results confirmed that, when a system including the 3'UTR of CDK2 wild-type DNA was transfected with pre-miR-124a, the luciferase activity was remarkably suppressed. The fact confirmed that, in the expression of CDK2, miR-124a was directly involved in the suppression of the expression of the 3'UTR of mRNA.

Experimental Example 7

Influences of miR-124a on Expression of Inflammatory Protein in RA-FLS Cells

In a system transfected with pre-miR-124a and a system transfected with control pre-miRNA in the same manner as in Example 1 and Experimental Example 1, actions on the expression of IL-8, vascular endothelial growth factor (VEGF), angiogenin as an angiogenic factor, and monocyte chemotactic protein-1 (MCP1) were confirmed. The amount of each factor was measured by an ELISA system.

Figure 15:
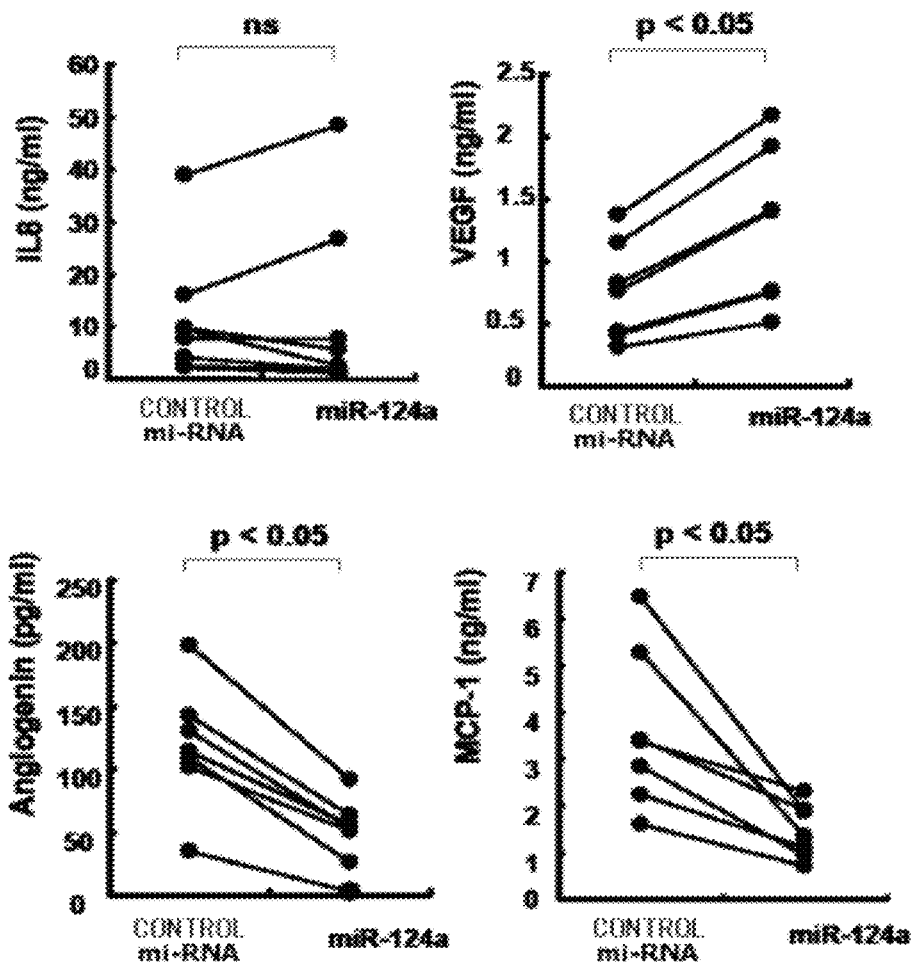
FIG. 15 are graphs illustrating influences of miR-124a on the expression of MCP1 in various RA-FLSs (Experimental Example 7).

The results showed that, in the system transfected with pre-miR-124a, there was no significant difference in the expression of IL-8, whereas the expression of VEGF showed an increasing tendency, and the expression of angiogenin and MCP-1 showed a decreasing tendency (FIG. 15).

Experimental Example 8

Influences of miR-124a on Expression of MCP1

By the same technique as in Experimental Example 5, with regard to the expression of an MCP1 protein in E11 cells, the action of miR-124a on the 3'-untranslated region (3'UTR) of mRNA was confirmed by a luciferase assay. A study was made by incorporating the 3' UTR of MCP1 DNA into a luciferase expression vector (psiCHECK™ vector (Promega)) and introducing the resultant into E11 cells. A system in which part of genes in the 3'UTR of MCP1 DNA were altered was used as a control for the 3'UTR (mutant-type). A system in which the 3'UTR of MCP1 wild-type DNA was bound and a system in which the 3'UTR of MCP1 mutant-type DNA was bound were introduced into E11 cells, and systems transfected with various pre-miRNAs were examined based on a luciferase activity. A luciferase activity was examined in each of controls, i.e., a system in which no pre-miRNA was added and a system in which control pre-miRNA was added in the same manner as in Example 1.

MCP1 DNA is as set forth in GenBank accession No. AF519531, and part of the 3'UTR (Positions 5596 to 5981) of MCP1 wild-type DNA was amplified by a PCR method using primers having sequences set forth in the following SEQ ID NOS:

```
MCP1-F-XhoI:
CTCGAGtccccagacaccctgttta      (SEQ ID NO: 6)
(Positions 5648 to 5667);
and MCP1-R-Not I:
GCGGCCGCcaaaacatcccaggggtaga   (SEQ ID NO: 7)
(Positions 5846 to 5827).
```

The 3'UTR portion of MCP1 mutant-type DNA was produced by a PCR method using primers having the following sequences:

```
MCP1-3'UTR-mut-F:
acattatCGcttaagtaatgttaattc;   (SEQ ID NO: 8)
and

MCP1-3'UTR-mut-R:
cttaagCGataatgtttcacatcaac.    (SEQ ID NO: 9)
```

Figure 16:
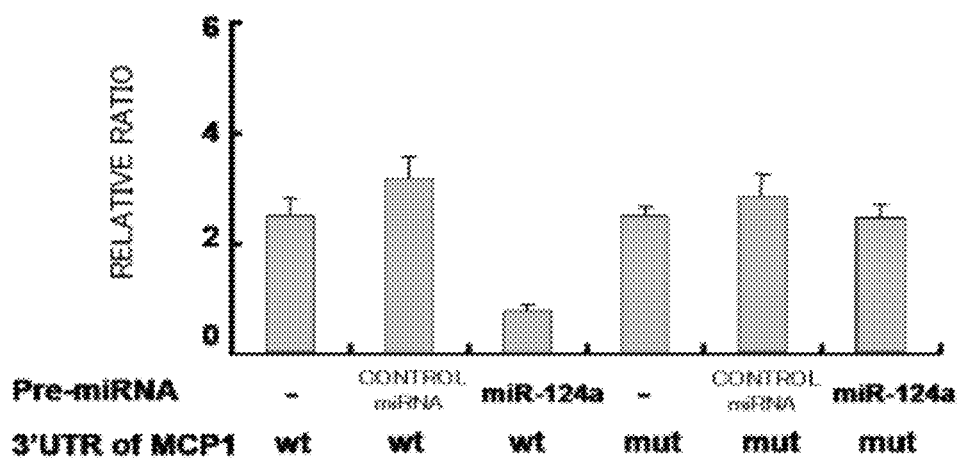
FIG. 16 is a graph illustrating influences of miR-124a on an mRNA non-coding 3'-region of MCP1 (Experimental Example 8).

Measurement results under the respective conditions were each expressed as a relative ratio with respect to a luciferase activity for a control, which had been incorporated into a vector, defined as 1 (FIG. 16). The results confirmed that, when a system including the 3'UTR of MCP1 wild-type DNA was transfected with pre-miR-124a, the luciferase activity was remarkably suppressed. The fact confirmed that, in the expression of MCP1, miR-124a was directly involved in the suppression of the expression of the 3'UTR of mRNA.

Experimental Example 9

Influences (1) of miR-124a on Expression of CDK6 in Cells

A study was made to determine what protein in cells is affected by miR-124a to arrest cell cycles at the G1 phase and suppress the growth of cells. Here, the study was made with a focus on a CDK6 protein which functions throughout the G1 phase to the S phase.

Influences on the expression of a CDK6 protein in the case where RA-FLS (RA20) cells and E11 cells were transfected with pre-miR-124a in the same manner as in Example 1 and Experimental Example 1, and cultured in a $CO_2$ incubator for 72 hours were examined by a western blotting method. The mouse anti-human CDK6 antibody clone used was one manufactured by Cell Signaling Technology. The expression amount of actin serving as a housekeeping protein for confirming the expression of the protein was also confirmed.

Figure 17:
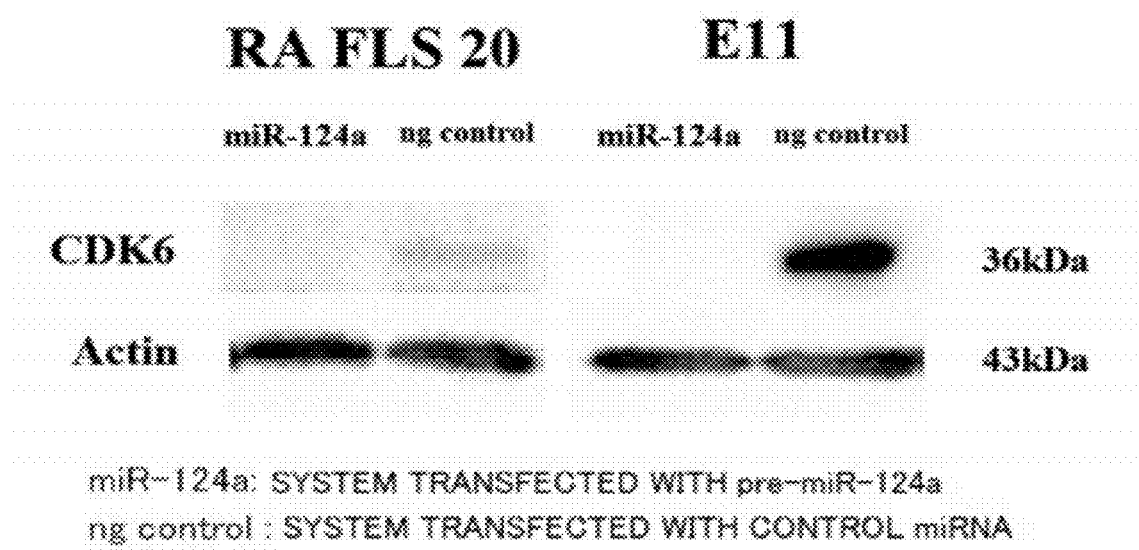
FIG. 17 are photographs showing influences of miR-124a on the expression of CDK6 in RA-FLS RA20 cells and E11 cells (Experimental Example 9).

The results confirmed that, in the transfection with pre-miR-124a, the expression of CDK6 was suppressed in the respective cells as compared to the control (FIG. 17). Those results and the results of Experimental Examples 4 to 6 confirmed that the expression of cyclin-dependent kinase called CDK6 and CDK2, which had a relationship with the progression of the G1 phase and the initiation of the S phase in mammals, was suppressed by the presence of miR-124a, suggesting that miR-124a was able to regulate the cell cycles of synovial cells and suppress the growth of synovial cells.

INDUSTRIAL APPLICABILITY

As mentioned in detail above, the marker for rheumatoid arthritis of the present invention is non-coding RNA whose expression is specifically increased or decreased in rheumatoid arthritis. In particular, mi-RNA (miR-124a) whose expression is specifically suppressed in rheumatoid arthritis may serve as an effective marker. There can be provided an inspection method using miR-124a as an indicator because the expression of miR-124a is decreased in rheumatoid arthritis-associated cells.

In addition, the decrease of miR-124a as mi-RNA which can function as the marker of the present invention is presumably associated with the pathology of rheumatoid arthritis. In view of the foregoing, an oligonucleotide containing miR-124a can suppress CDK2, CDK6, and MCP1, suppress the inflammation and growth of RA synovial cells attributed to those proteins, and thus act as an active ingredient for the treatment of rheumatoid arthritis. Accordingly, a formulation obtained by mixing miR-124a as an active ingredient with, for example, a pharmaceutically acceptable carrier, diluent, excipient, and stabilizing agent may be utilized as the therapeutic agent for rheumatoid arthritis.

The invention claimed is:

1. A therapeutic method for rheumatoid arthritis comprising administering to a subject in need thereof a therapeutic agent comprising an oligonucleotide as an active ingredient formed of a base sequence selected from the following:

```
(1) UUAAGGCACGCGGUGAAUGCCA     (SEQ ID NO: 1);
and (2) UAAGGCACGCGGUGAAUGCC       (SEQ ID NO: 10).
```

2. The therapeutic method for rheumatoid arthritis according to claim 1, wherein administration of the therapeutic agent is performed after inspecting the subject for rheumatoid arthritis by using an indicator marker of rheumatoid arthritis.

3. The therapeutic method for rheumatoid arthritis according to claim 1, further comprising quantifying a value of the indicator marker of rheumatoid arthritis in the subject and diagnosing the subject with rheumatoid arthritis if the quantified value is lower than that of a value for the indicator marker in a subject free of rheumatoid arthritis.

4. The therapeutic method for rheumatoid arthritis according to claim 3, wherein the indicator marker of rheumatoid arthritis has a base sequence selected from the following:

```
(1) UUAAGGCACGCGGUGAAUGCCA     (SEQ ID NO: 1);
and (2) UAAGGCACGCGGUGAAUGCC       (SEQ ID NO: 10).
```

* * * * *

SEQUENCE LISTING

<160> NUMBER OF SEQ ID NOS: 10

<210> SEQ ID NO 1
<211> LENGTH: 22
<212> TYPE: RNA
<213> ORGANISM: Artificial
<220> FEATURE:
<223> OTHER INFORMATION: Synthesized RNA of miR-124a

<400> SEQUENCE: 1
uuaaggcacg cggugaaugc ca                                         22

<210> SEQ ID NO 2
<211> LENGTH: 26
<212> TYPE: DNA
<213> ORGANISM: Artificial
<220> FEATURE:
<223> OTHER INFORMATION: Synthesized primer for detecting human CDK gene

<400> SEQUENCE: 2
ctcgagccct ttcttccagg atgtga                                     26

<210> SEQ ID NO 3
<211> LENGTH: 28
<212> TYPE: DNA
<213> ORGANISM: Artificial
<220> FEATURE:
<223> OTHER INFORMATION: Synthesized primer for detecting human CDK gene

<400> SEQUENCE: 3
gcggccgctg ttcaccgtca gcactagc                                   28

<210> SEQ ID NO 4
<211> LENGTH: 27
<212> TYPE: DNA
<213> ORGANISM: Artificial
<220> FEATURE:
<223> OTHER INFORMATION: Synthesized primer for generating human CDK2
      3'UTR mutation

<400> SEQUENCE: 4
tgaacttcgc ttaaacactc accttct                                    27

<210> SEQ ID NO 5
<211> LENGTH: 26
<212> TYPE: DNA
<213> ORGANISM: Artificial
<220> FEATURE:
<223> OTHER INFORMATION: Synthesized primer for generating human CDK2
      3'UTR mutation

<400> SEQUENCE: 5
tttaagcgaa gttcagaggg cccacc                                     26

<210> SEQ ID NO 6
<211> LENGTH: 26
<212> TYPE: DNA
<213> ORGANISM: Artificial
<220> FEATURE:
<223> OTHER INFORMATION: Synthesized primer for detecting human MCP1
      gene

<400> SEQUENCE: 6
ctcgagtccc cagacaccct gtttta                                     26

<210> SEQ ID NO 7
<211> LENGTH: 28
<212> TYPE: DNA
<213> ORGANISM: Artificial

```
<220> FEATURE:
<223> OTHER INFORMATION: Synthesized primer for detecting human MCP1
      gene

<400> SEQUENCE: 7
gcggccgcca aaacatccca ggggtaga                                          28

<210> SEQ ID NO 8
<211> LENGTH: 27
<212> TYPE: DNA
<213> ORGANISM: Artificial
<220> FEATURE:
<223> OTHER INFORMATION: Synthesized primer for generating human MCP1
      3'UTR mutation

<400> SEQUENCE: 8
acattatcgc ttaagtaatg ttaattc                                           27

<210> SEQ ID NO 9
<211> LENGTH: 26
<212> TYPE: DNA
<213> ORGANISM: Artificial
<220> FEATURE:
<223> OTHER INFORMATION: Synthesized primer for generating human MCP1
      3'UTR mutation

<400> SEQUENCE: 9
cttaagcgat aatgtttcac atcaac                                            26

<210> SEQ ID NO 10
<211> LENGTH: 20
<212> TYPE: RNA
<213> ORGANISM: Artificial
<220> FEATURE:
<223> OTHER INFORMATION: Synthesized RNA of miR-124

<400> SEQUENCE: 10
uaaggcacgc ggugaaugcc                                                   20
```